(12) United States Patent
Cheng et al.

(10) Patent No.: US 9,741,969 B2
(45) Date of Patent: Aug. 22, 2017

(54) CARRIER GENERATION MATERIAL AND ORGANIC LIGHT-EMITTING DIODE

(71) Applicant: NATIONAL TSING HUA UNIVERSITY, Hsinchu (TW)

(72) Inventors: Chien-Hong Cheng, Hsin-Chu (TW); Wei-Ting Hsieh, Hsinchu (TW); Chen-Hsun Hung, Hsinchu (TW); Min-Jie Huang, Hsinchu (TW); Cheng-Chang Lai, Hsinchu (TW); Chuang-Yi Liao, Hsinchu (TW)

(73) Assignee: National Tsing Hua University, Hsinchu (TW)

( * ) Notice: Subject to any disclaimer, the term of this patent is extended or adjusted under 35 U.S.C. 154(b) by 150 days.

(21) Appl. No.: 14/860,559

(22) Filed: Sep. 21, 2015

(65) Prior Publication Data

US 2017/0062771 A1 Mar. 2, 2017

(30) Foreign Application Priority Data

Aug. 24, 2015 (TW) .............................. 104127446 A

(51) Int. Cl.
*H01L 51/54* (2006.01)
*H01L 51/52* (2006.01)
(Continued)

(52) U.S. Cl.
CPC ........ *H01L 51/5278* (2013.01); *C07D 241/42* (2013.01); *C07D 241/44* (2013.01);
(Continued)

(58) Field of Classification Search
CPC ............... H01L 51/0032; H01L 51/005; H01L 51/0072; H01L 51/0071; H01L 51/50;
(Continued)

(56) References Cited

U.S. PATENT DOCUMENTS

| 495,625 A | 4/1893 | Cotton |
| 4,446,217 A | 5/1984 | Takasu et al. |

(Continued)

FOREIGN PATENT DOCUMENTS

| CN | 1347572 A | 5/2002 |
| CN | 1376758 A | 10/2002 |

(Continued)

OTHER PUBLICATIONS

Smith et al. J. Am. Chem. Soc. 1939, 61, 2619-2624. Year of publication: 1939.*

(Continued)

*Primary Examiner* — Andrew K Bohaty

(57) ABSTRACT

A carrier generation material is provided, which has a chemical structure of:

wherein $R^1$ is hydrogen or alkyl group; each of $R^2$ is independently hydrogen, halogen, —CN, —$CF_3$, —$NO_2$, or alkyl group; each of $R^3$ is independently hydrogen, halogen, —CN, —$CF_3$, —$NO_2$, or alkyl group; $R^4$ is hydrogen, halogen, —CN, —$CF_3$, —$NO_2$, or alkyl group; $R^5$ is hydrogen, halogen, —CN, —$CF_3$, —$NO_2$, or alkyl group; $R^6$ is =O, =NH, or malononitrile group, and $R^7$ is hydrogen, halogen, —CN, —$CF_3$, —$NO_2$, or alkyl group.

4 Claims, 1 Drawing Sheet

(51) Int. Cl.
| | | |
|---|---|---|
| *C07D 241/46* | (2006.01) | |
| *C07D 241/44* | (2006.01) | |
| *C07D 487/04* | (2006.01) | |
| *C07D 241/42* | (2006.01) | |
| *H01L 51/00* | (2006.01) | |

(52) U.S. Cl.
CPC ......... *C07D 241/46* (2013.01); *C07D 487/04* (2013.01); *H01L 51/0072* (2013.01)

(58) Field of Classification Search
CPC . H01L 51/5278; C07D 241/42; C07D 241/44; C07D 241/46; C07D 487/00; C07D 487/02; C07D 487/04; C07D 487/10
USPC ....... 428/690, 691, 411.4, 336, 917; 427/58, 427/66; 313/500–512; 257/40, 88–104, 257/E51.001–E51.052; 252/301.16–301.35
See application file for complete search history.

(56) References Cited

U.S. PATENT DOCUMENTS

| | | | |
|---|---|---|---|
| 5,077,142 A * | 12/1991 | Sakon | C09K 11/06 313/504 |
| 5,248,579 A | 9/1993 | Terrell et al. | |
| 5,306,587 A | 4/1994 | Terrell et al. | |
| 5,585,213 A | 12/1996 | Tamano et al. | |
| 7,875,879 B2 | 1/2011 | Suzuki et al. | |
| 7,911,135 B2 | 3/2011 | Sakata et al. | |
| 7,927,720 B2 | 4/2011 | Nomura et al. | |
| 7,931,974 B2 | 4/2011 | Egawa et al. | |
| 7,951,470 B2 | 5/2011 | Tokuda et al. | |
| 7,993,761 B2 | 8/2011 | Osaka et al. | |
| 8,008,489 B2 | 8/2011 | Egawa et al. | |
| 8,119,259 B2 | 2/2012 | Kadoma et al. | |
| 8,178,216 B2 | 5/2012 | Nomura et al. | |
| 8,203,262 B2 | 6/2012 | Seo et al. | |
| 8,216,696 B2 | 7/2012 | Kawakami et al. | |
| 8,252,433 B2 | 8/2012 | Egawa et al. | |
| 8,313,845 B2 | 11/2012 | Nomura et al. | |
| 8,314,101 B2 | 11/2012 | Kadoma et al. | |
| 8,362,472 B2 | 1/2013 | Suzuki et al. | |
| 8,471,017 B2 | 6/2013 | Egawa et al. | |
| 8,507,901 B2 | 8/2013 | Pan | |
| 8,703,305 B2 | 4/2014 | Egawa et al. | |
| 8,815,412 B2 | 8/2014 | Kadoma et al. | |
| 8,927,117 B2 | 1/2015 | Buesing et al. | |
| 2005/0089789 A1 | 4/2005 | Zhu | |
| 2007/0222374 A1 | 9/2007 | Egawa et al. | |
| 2007/0228938 A1* | 10/2007 | Hatwar | H01L 27/3213 313/504 |
| 2008/0079354 A1 | 4/2008 | Egawa et al. | |
| 2008/0091012 A1 | 4/2008 | Egawa et al. | |
| 2008/0193797 A1 | 8/2008 | Heil et al. | |
| 2011/0180791 A1 | 7/2011 | Pan et al. | |
| 2011/0284835 A1 | 11/2011 | Osaka et al. | |
| 2011/0297925 A1 | 12/2011 | Breuning | |
| 2012/0097899 A1 | 4/2012 | Parham et al. | |
| 2012/0243909 A1 | 9/2012 | Tomari et al. | |
| 2012/0256172 A1* | 10/2012 | Ito | C07D 493/04 257/40 |
| 2012/0302751 A1 | 11/2012 | Nomura et al. | |
| 2012/0313506 A1 | 12/2012 | Egawa et al. | |
| 2013/0049577 A1 | 2/2013 | Kadoma et al. | |
| 2013/0053558 A1 | 2/2013 | Pflumm et al. | |
| 2013/0306959 A1 | 11/2013 | Ikeda et al. | |
| 2014/0001451 A1 | 1/2014 | Mizuki et al. | |
| 2014/0228566 A1 | 8/2014 | Egawa et al. | |

FOREIGN PATENT DOCUMENTS

| | | | |
|---|---|---|---|
| CN | 1487937 A | | 4/2004 |
| CN | 1554726 A | | 12/2004 |
| CN | 1585152 A | | 2/2005 |
| CN | 1634927 A | | 7/2005 |
| CN | 1725455 A | | 1/2006 |
| CN | 1828963 A | | 9/2006 |
| CN | 102150086 A | | 8/2011 |
| CN | 102762630 A | | 10/2012 |
| CN | 103403906 A | | 11/2013 |
| CN | 104205391 A | | 12/2014 |
| JP | 09003342 A | * | 1/1997 |
| TW | 200526759 | | 8/2005 |
| TW | 200824498 | | 6/2008 |
| TW | 201144313 | | 12/2011 |
| TW | 201244211 | | 11/2012 |
| TW | 201315729 | | 4/2013 |
| TW | 201345896 | | 11/2013 |
| TW | I425074 | | 2/2014 |
| TW | I435889 | | 5/2014 |
| TW | 201428083 | | 7/2014 |
| TW | I461506 | | 11/2014 |

OTHER PUBLICATIONS

Machine translation of JP09-003342. Date of publication: Jan. 7, 1997.*

* cited by examiner

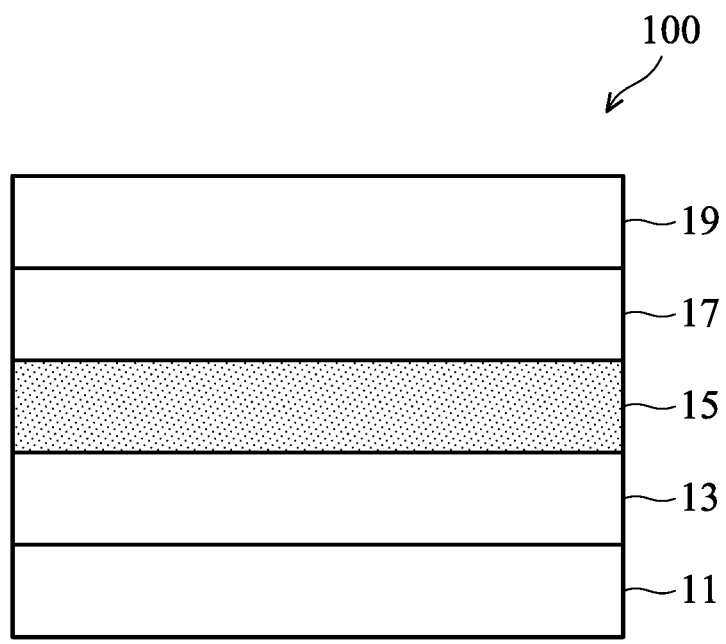

CARRIER GENERATION MATERIAL AND ORGANIC LIGHT-EMITTING DIODE

CROSS REFERENCE TO RELATED APPLICATIONS

This Application claims priority of Taiwan Patent Application No. 104127446, filed on Aug. 24, 2015, the entirety of which is incorporated by reference herein.

BACKGROUND

Technical Field

The disclosure relates to an organic light-emitting diode, and in particular it relates to the composition of a carrier generation layer thereof.

Description of the Related Art

Compared to inorganic compounds, organic compounds are more varied in terms of their material system. Organic materials with any function can be synthesized through the appropriate molecular designs. The films of organic compounds have extremely high flexibility and excellent processability. In recent years, functional organic materials with the above advantages have attracted attention among those in the photonics and electronics industries.

Because organic compounds are inherently free of carriers, they normally have excellent insulative properties. In the electronics field, these organic compounds generally served as insulators, being used in insulation materials, protection materials, encapsulation materials, etc. However, a mechanism wherein a large current flows through organic materials was initially developed in the electronics field. For example, organic films with a total thickness of about 100 nm can be disposed between electrodes. Organic hole transport layers and organic electron transport layers are stacked to constitute a stack of the organic films, and a light-emitting material (phosphorescent material) may serve as an electron-hole combination layer in the stack. By applying a voltage to a device, the electrons and holes can be combined in the light-emitting layer to emit light. As such, the device is a so-called organic light-emitting diode (OLED).

Some related art provides the concept of a carrier generation layer to improve the luminescent efficiency of the OLED, in which an anode, a first electroluminescent layer, a carrier generation layer, a second electroluminescent layer, and a cathode are sequentially stacked. Note that the electroluminescent layer (EL layer) means an organic compound layer, and it may emit light by injecting carriers. In addition, the carrier generation layer is a floating electrode without a connection to an outer circuit.

When a voltage V is applied through the anode and the cathode of the OLED, the carrier generation layer may produce electrons and holes, wherein the electrons are injected into the first EL layer and the holes are injected into the second EL layer. Compared to an OLED with only one EL layer, the OLED with two EL layers may emit double the amount of luminescence using the same current (but using double or higher voltage).

The OLED with the carrier generation layer may enhance the current efficiency and lower the current density several-fold by stacking a plurality of EL layers. Theoretically, the device lifetime should be elongated by the enhanced current efficiency due to lowered current density. However, the selection of the carrier generation material is rare, due to late development. Accordingly, a novel carrier generation material is called for to increase the enablement of the carrier generation material in the OLED.

BRIEF SUMMARY

One embodiment of the disclosure provides a carrier generation material, having a chemical structure of:

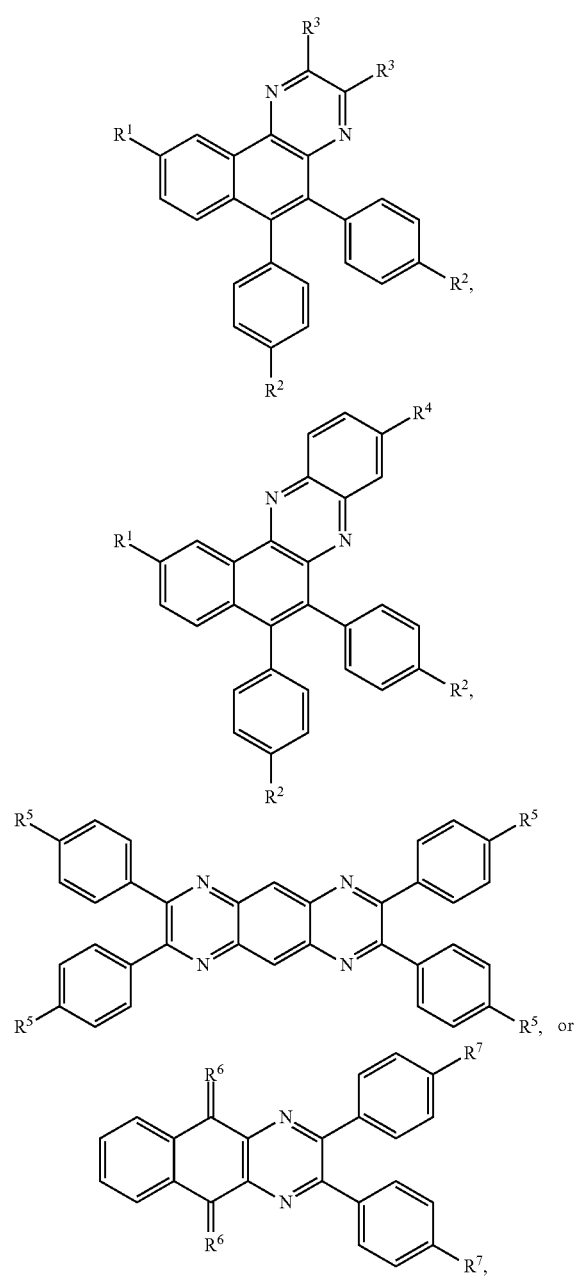

wherein $R^1$ is hydrogen or alkyl group; each of $R^2$ is independently hydrogen, halogen, —CN, —CF$_3$, —NO$_2$, or alkyl group; each of $R^3$ is independently hydrogen, halogen, —CN, —CF$_3$, —NO$_2$, or alkyl group; $R^4$ is hydrogen, halogen, —CN, —CF$_3$, —NO$_2$, or alkyl group; $R^5$ is hydrogen, halogen, —CN, —CF$_3$, —NO$_2$, or alkyl group; $R^6$ is =O, =NH, or malononitrile group; and $R^7$ is hydrogen, halogen, —CN, —CF$_3$, —NO$_2$, or alkyl group.

One embodiment of the disclosure provides an organic light-emitting diode, comprising: an anode; a cathode; a carrier generation material layer, including the described carrier generation material, disposed between the anode and the cathode; a first light-emitting layer disposed between the anode and the carrier generation material layer; and a second light-emitting layer, disposed between the cathode and the carrier generation material layer.

A detailed description is given in the following embodiments with reference to the accompanying drawings.

BRIEF DESCRIPTION OF THE DRAWINGS

The disclosure can be more fully understood by reading the subsequent detailed description and examples with references made to the accompanying drawings, wherein:

The FIGURE shows an organic light-emitting diode in one embodiment of the disclosure.

DETAILED DESCRIPTION

The following description is of the best-contemplated mode of carrying out the disclosure. This description is made for the purpose of illustrating the general principles of the disclosure and should not be taken in a limiting sense. The scope of the disclosure is best determined by reference to the appended claims.

In one embodiment, a carrier generation material has a chemical structure of Formula 1. In Formula 1, $R^1$ is hydrogen or alkyl group. Each of $R^2$ is independently hydrogen, halogen, —CN, —CF$_3$, —NO$_2$, or alkyl group. Each of $R^3$ is independently hydrogen, halogen, —CN, —CF$_3$, —NO$_2$, or alkyl group.

(Formula 1)

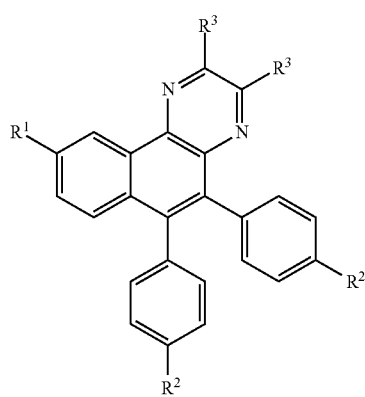

The carrier generation material of Formula 1 can be synthesized as described below. First, a compound should be pre-synthesized as shown in Formula 2. In Formula 2, $R^1$ can be varied by selecting commercially available raw materials or processing general chemical reactions, and the related description is omitted here for simplifying the description.

(Formula 2)

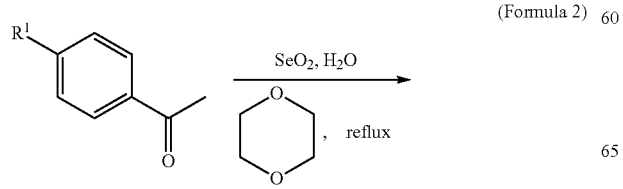

-continued

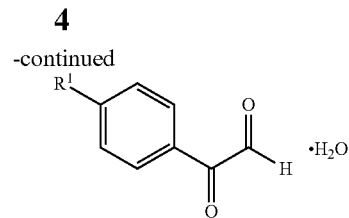

Subsequently, the product in Formula 2 is reacted with an alkyne compound, as shown in Formula 3. In Formula 3, $R^2$ can be varied by selecting commercially available raw materials or processing general chemical reactions, and the related description is omitted here for simplifying the description.

(Formula 3)

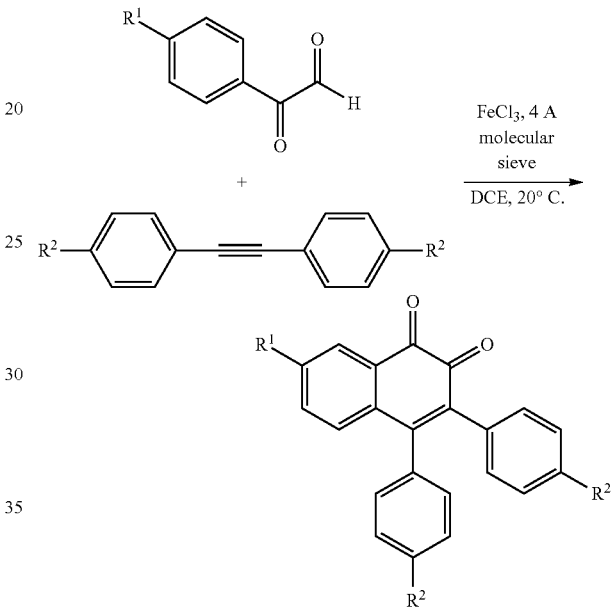

The product in Formula 3 is then reacted with a diamine compound to form a compound of Formula 1, as shown in Formula 4. In Formula 4, $R^3$ can be varied by selecting commercially available raw materials or processing general chemical reactions, and the related description is omitted here for simplifying the description.

(Formula 4)

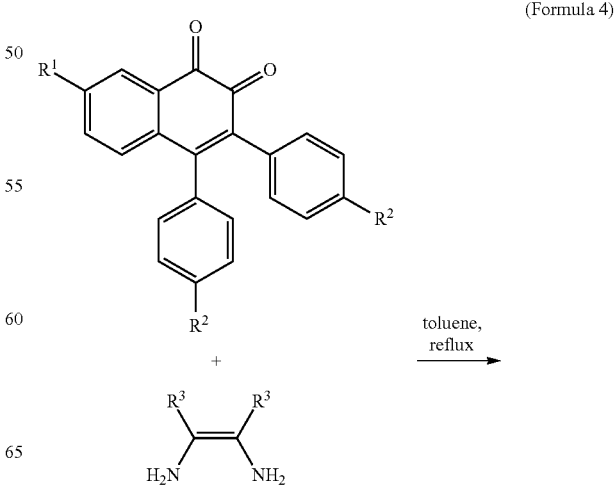

(Formula 5)

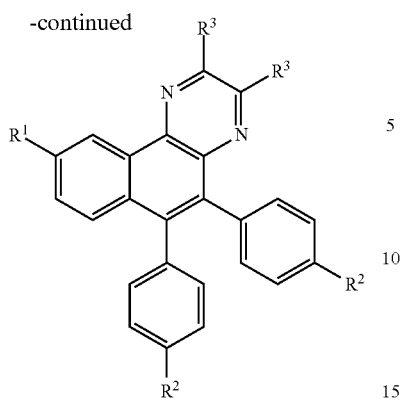

In one embodiment, the carrier generation material has a chemical structure of Formula 5. In Formula 5, $R^1$ is hydrogen or alkyl group. Each of $R^2$ is independently hydrogen, halogen, —CN, —CF$_3$, —NO$_2$, or alkyl group. $R^4$ is hydrogen, halogen, —CN, —CF$_3$, —NO$_2$, or alkyl group.

(Formula 6)

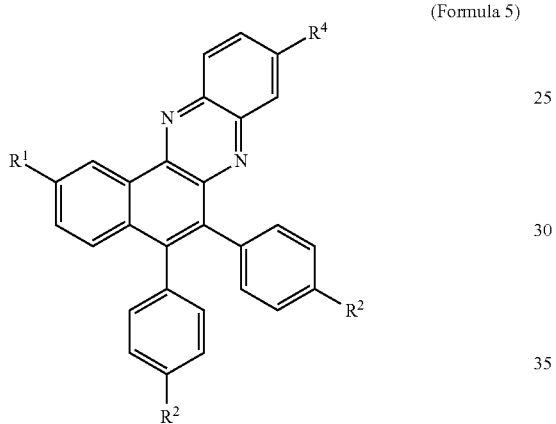

The carrier generation material of Formula 5 can be synthesized as below. The product in Formula 3 is reacted with a diamine compound to form the compound of Formula 5, as shown in Formula 6. In Formula 6, $R^4$ can be varied by selecting commercially available raw materials or processing general chemical reactions, and the related description is omitted here for simplifying the description.

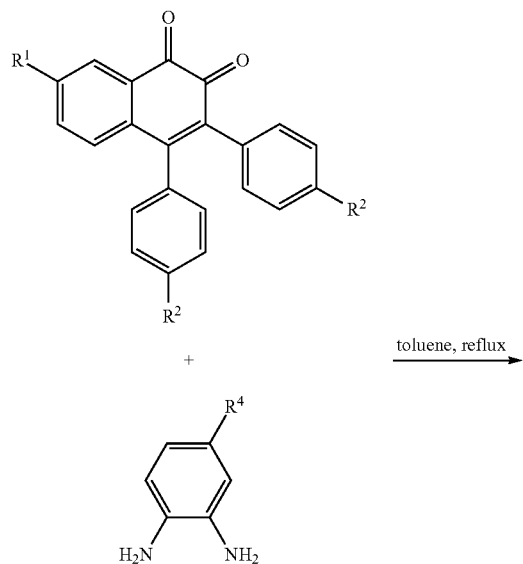

(Formula 7)

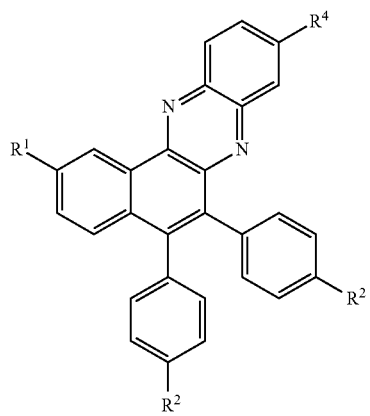

In one embodiment, the carrier generation material has a chemical structure of Formula 7. In Formula 7, $R^5$ is hydrogen, halogen, —CN, —CF$_3$, —NO$_2$, or alkyl group.

The carrier generation material of Formula 7 can be synthesized as below. An ethanedione compound and a tetramine compound are reacted to form the product of Formula 7, as shown in Formula 7. In Formula 8, $R^5$ can be varied by selecting commercially available raw materials or processing general chemical reactions, and the related description is omitted here for simplifying the description.

(Formula 8)

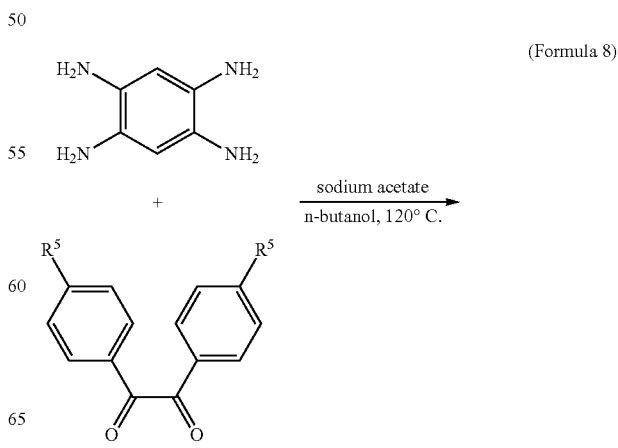

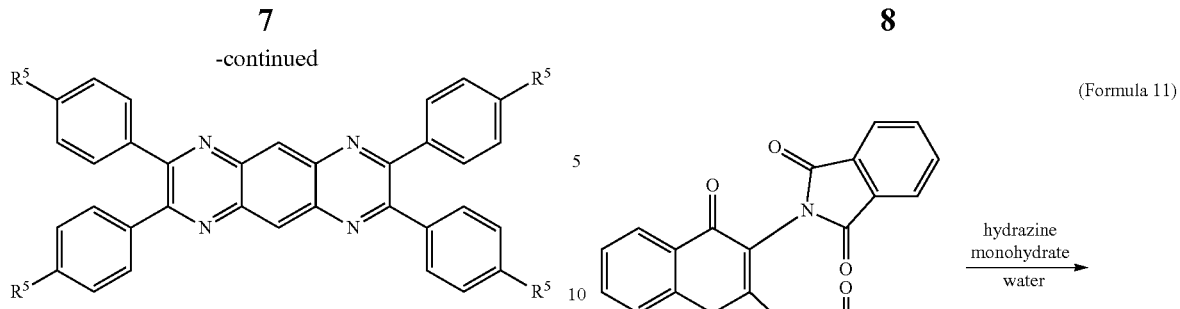

In one embodiment, the carrier generation material has a chemical structure of Formula 9. In Formula 9, $R^6$ is =O, =NH, or malononitrile group. $R^7$ is hydrogen, halogen, —CN, —$CF_3$, —$NO_2$, or alkyl group.

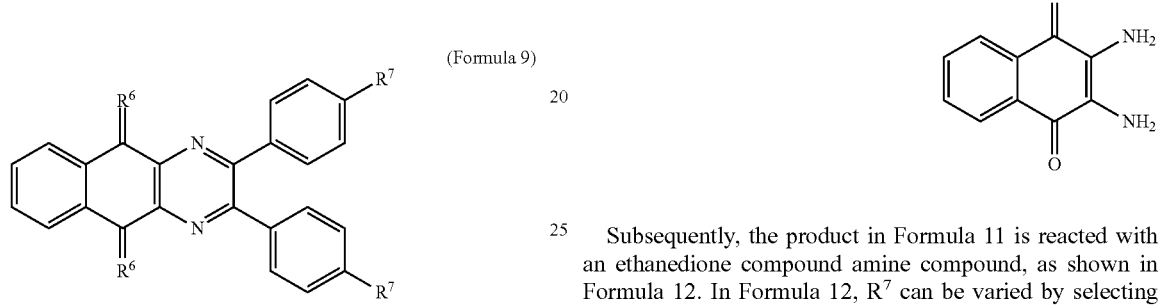

The carrier generation material of Formula 9 can be synthesized as below. First, 2,3-dichloro-1,4-naphthoquinone is reacted with phthalimide salt, as shown in Formula 10.

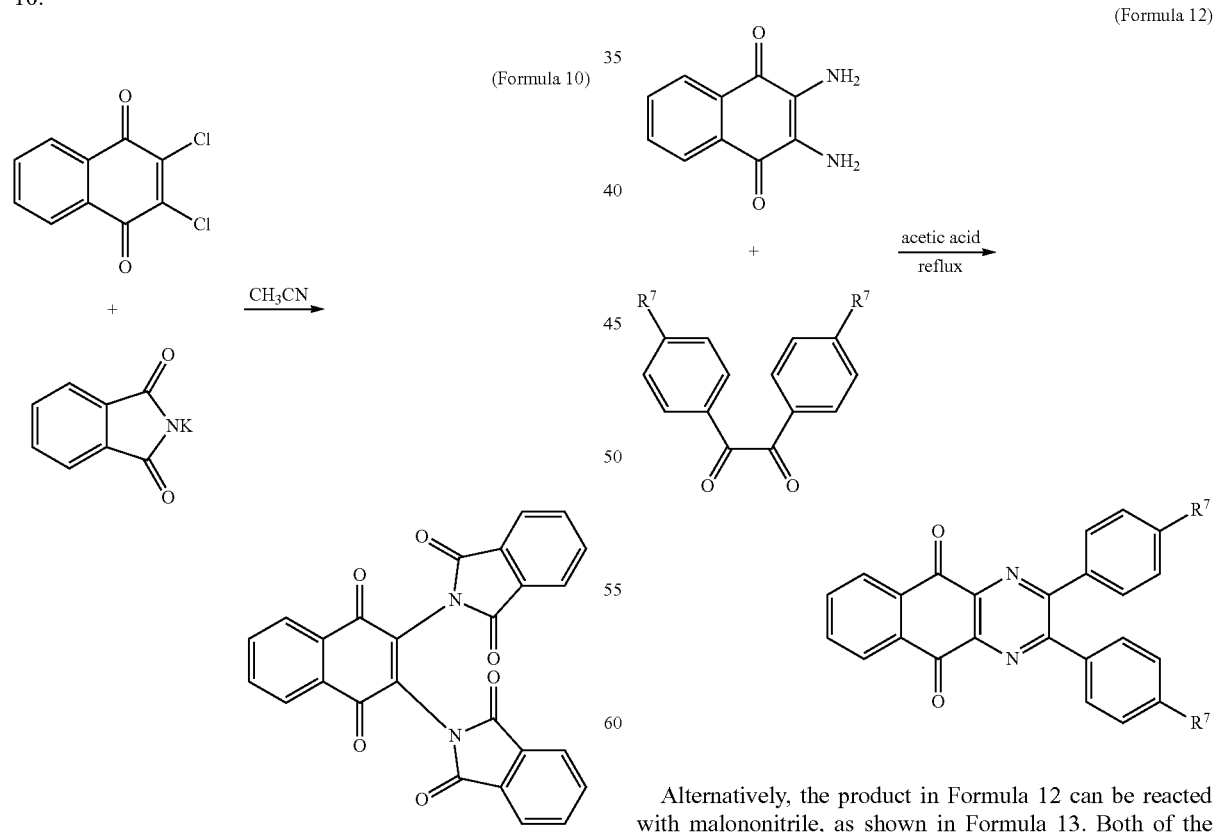

Subsequently, the product in Formula 10 is reacted with hydrazine monohydrate, as shown in Formula 11.

Subsequently, the product in Formula 11 is reacted with an ethanedione compound amine compound, as shown in Formula 12. In Formula 12, $R^7$ can be varied by selecting commercially available raw materials or processing general chemical reactions, and the related description is omitted here for simplifying the description.

Alternatively, the product in Formula 12 can be reacted with malononitrile, as shown in Formula 13. Both of the products in Formulae 12 and 13 belong to the compound of Formula 9, and the difference therebetween is R6 being =O or malononitrile group.

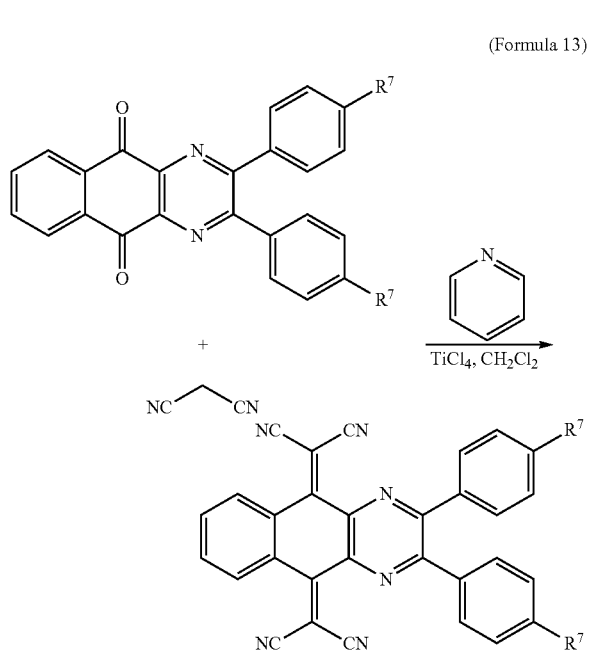

(Formula 13)

The above carrier generation materials can be applied in OLEDs. As shown in the FIGURE, the OLED 100 may include an anode 11, a cathode 19, and a carrier generation material layer 15 disposed therebetween. The OLED 100 also includes a first light-emitting layer 13 disposed between the anode 11 and the carrier generation material layer 15, and a second light-emitting layer 17 disposed between the cathode 19 and the carrier generation material layer 15.

In one embodiment, the anode 11 has a thickness of about 15 nm. The anode 11 can be a transparent conductive material such as indium tin oxide (ITO), indium zinc oxide (IZO), aluminum zinc oxide (AZO), cadmium tin oxide (CTO), tin oxide (SnO2), zinc oxide (ZnO), or the like. The cathode 19 may have a thickness of 75 nm to 100 nm. The cathode can be composed of composition of magnesium aluminum alloy, magnesium silver alloy, magnesium indium alloy, aluminum lithium alloy, or aluminum. The first light-emitting layer 13 may have a thickness of 120 nm to 140 nm. The first light-emitting layer can be composed of N,N'-diphenyl-1-naphthaleny-1,1'-biphenyl-4,4'-diamine, 4,4',4"-Tris(carbazol-9-yl)-triphenylamine, 9,9-(1,3-phenylene)bis-9H-carbazole, tris(2-phenylpyridine)iridium, tris[1-phenylisoquinoline-C2,N]iridium(III) (Ir(piq)3), bis[2-(4,6-difluorophenyl)pyridinato-C2,N](picolinato)iridium(III), 1,3,5-tris(1-phenyl-1H-benzimidazol-2-yl)benzene, 3,3'-[5'-[3-(3-Pyridinyl)phenyl][1,1':3',1"-terphenyl]-3,3"-diyl]bispyridine, co-evaporated lithium fluoride and electron transport layer, or aluminum. The second light-emitting layer 17 may have a thickness of 120 nm to 140 nm. The second light-emitting layer can be composed of N,N'-diphenyl-1-naphthaleny-1,1'-biphenyl-4,4'-diamine, 4,4',4"-Tris(carbazol-9-yl)-triphenylamine, 9,9-(1,3-phenylene)bis-9H-carbazole, tris(2-phenylpyridine)iridium, Ir(piq)3, bis[2-(4,6-difluorophenyl)pyridinato-C2,N](picolinato)iridium(III), 1,3,5-tris(1-phenyl-1H-benzimidazol-2-yl)benzene, or 3,3'-[5'-[3-(3-Pyridinyl)phenyl][1,1':3',1"-terphenyl]-3,3"-diyl]bispyridine. The carrier generation material layer 15 may have a thickness of 1 nm to 5 nm. The carrier generation material layer 15 can be composed of the compound of Formula 1, Formula 5, Formula 7, or Formula 9.

The OLED 100 may further include other common layered materials such as an electron injection layer, a hole injection layer, an electron transport layer, a hole transport layer, a hole block layer, other functional layer, or a combination thereof if necessary. Alternatively, the OLED 100 may include a plurality of carrier generation layer, and the number of the light-emitting layers is the number of the carrier generation layer add one (+1), wherein at least one of the carrier generation layer is composed of the compound of Formula 1, Formula 5, Formula 7, or Formula 9.

Below, exemplary embodiments will be described in detail with reference to the accompanying drawings so as to be easily realized by a person having ordinary knowledge in the art. The inventive concept may be embodied in various forms without being limited to the exemplary embodiments set forth herein. Descriptions of well-known parts are omitted for clarity, and like reference numerals refer to like elements throughout.

EXAMPLES

Example 1

SeO$_2$ (8 g, 72 mmol) and water (1 g, 55 mol) were put into a two neck bottle (100 mL). 40 mL of 1,4-dioxane was then added into the bottle, and the mixture was heated to reflux for dissolving the SeO$_2$. 4-methyl-acetophenon (5.37 g, 40 mmol, and commercially available from Alfa Aesar) was then added into the bottle to react for 6 hours. The reaction result was filtered and washed by ethyl acetate to collect filtrate, and the organic solvent of the filtrate was removed by a rotary evaporator. The concentrated substance was re-crystallized by hot water to obtain 5.88 g of white solid (yield=88%). For details relating to the above reaction, refer to P. Wang, W.-J. Tao, X.-L. Sun, S. Liao, Y. Tang, *J. Am. Chem. Soc.*, 2013, 135, 16849-16852. The above reaction is shown in Formula 14. The spectra of the product in Formula 14 are listed below: $^1$H NMR (400 MHz, CDCl$_3$): δ 9.65 (s, 1H), 8.09 (d, J=8.4 Hz, 2H), 7.31 (d, J=8.0 Hz, 2H), 2.43 (s, 3H).

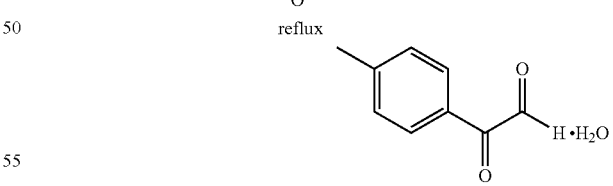

(Formula 14)

The product in Formula 14 (33.3 mg, 0.2 mmol), diphenylacetylene (42.8 mg, 0.24 mmol), and molecular sieves were put in a high-pressure tube. 0.5 mL of 1,2-dichloro ethane was added into the tube. Iron trichloride (97.4 mg, 0.6 mmol) was added into and dissolved by 1.5 mL of 1,2-dichloro ethane under nitrogen, and then added into the tube. The tube was vacuumed and purged by nitrogen, and the mixture in the tube was then reacted at room temperature for 1 hour. The reaction result was neutralized by 1 mL of water, and then filtered and washed by ethyl acetate to collect filtrate. The organic solvent of the filtrate was removed by a rotary evaporator. The concentrated substance was purified by chromatography with an eluent of ethyl acetate and n-hexane (v/v=1/4), thereby obtaining 39 mg of a red solid (yield=60%). The above reaction is shown in Formula 15. The spectra of the product in Formula 15 are listed below: $^1$H NMR (400 MHz, CDCl$_3$): δ 8.00 (s, 1H), 7.30-7.24 (m, 4H), 7.12-7.06 (m, 5H), 6.95-6.89 (m, 3H), 2.40 (s, 3H); $^{13}$C NMR (100 MHz, CDCl$_3$): δ 180.6 (CO), 179.3 (CO), 152.9 (C), 140.9 (C), 137.5 (C), 135.9 (CH), 135.7 (C), 134.1 (C), 133.5 (C), 130.9 (C), 130.8 (CH), 130.3 (2 CH), 130.2 (CH), 129.0 (2 CH), 128.1 (2 CH), 128.1 (CH), 127.4 (2 CH), 127.2 (CH), 21.0 (CH$_3$).

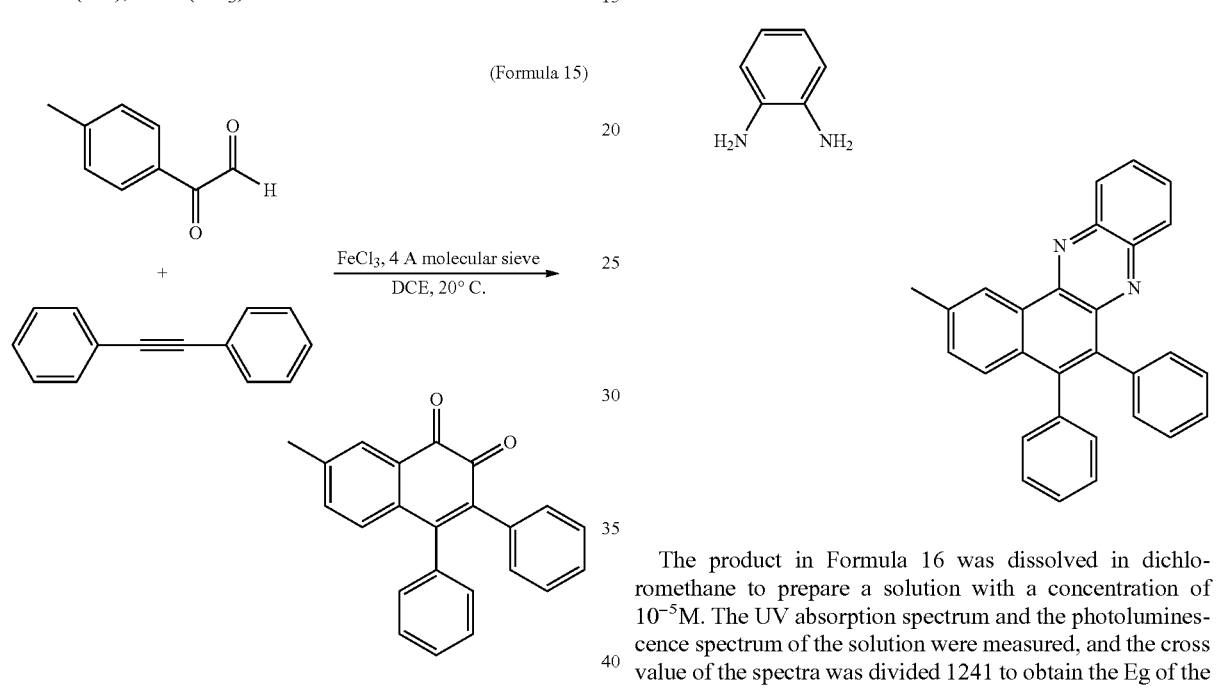

(Formula 15)

(Formula 16)

Example 2

The product of Formula 15 (324.4 mg, 1 mmol) and o-phenylenediamine (108.2 mg, 1 mmol) were put in a round-bottom bottle (100 mL). 40 mL toluene was then added into the bottle, and a Dean-Stark device was set on the bottle. The mixture in the bottle was refluxed and reacted under nitrogen. The organic solvent of the reaction result was removed by rotary evaporator, and the concentrated substance was dissolved by a small amount of ethyl acetate. The ethyl acetate solution was mixed with n-hexane for re-crystallization, thereby obtaining 361 mg of a pale yellow solid (yield=91%). The above reaction is shown in Formula 16. The spectra of the product in Formula 16 are listed below: $^1$H NMR (400 MHz, CDCl$_3$): δ 9.38 (s, 1H), 8.38 (d, J=8.4 Hz, 1H), 8.13 (d, J=8.4 Hz, 1H), 7.83 (t, J=8.4 Hz, 1H), 7.75 (t, J=8.4 Hz, 1H), 7.52-7.47 (m, 2H), 7.33-7.22 (m, 10H), 2.70 (s, 3H); $^{13}$C NMR (100 MHz, CDCl$_3$): δ 143.4 (C), 142.7 (2C), 141.8 (C), 141.3 (C), 138.6 (C), 137.7 (C), 137.7 (C), 136.4 (C), 131.7 (2 CH), 131.5 (C), 131.0 (CH), 130.8 (C), 130.7 (2 CH), 130.0 (CH), 129.7 (CH), 129.3 (CH), 129.2 (2 CH), 127.7 (2 CH), 127.7 (CH), 127.0 (2 CH), 126.9 (CH), 126.3 (CH), 125.1 (CH), 21.7 (CH$_3$).

The product in Formula 16 was dissolved in dichloromethane to prepare a solution with a concentration of $10^{-5}$M. The UV absorption spectrum and the photoluminescence spectrum of the solution were measured, and the cross value of the spectra was divided 1241 to obtain the Eg of the product in Formula 16 (2.7 eV).

The ultraviolet photoelectron spectrum (UPS) of the product in Formula 16 was measured to obtain the HOMO value of the product in Formula 16 (−7.5 eV). For details concerning the method of calculating the HOMO value from the UPS, refer to *Adv. Funct. Mater.*, 2012, 22, 600-608 and *J. Mater. Chem. C*, 2014, 2, 1982-1989. The LUMO value (−4.8 eV) can be obtained by subtracting the Eg from the HOMO value.

Example 3

4,4'-dibromobenzil (2 g, 5.4 mmol, and commercially available from Alfa Aesar) was put in a high-pressure tube. Copper (I) cyanide (1.07 g, 12 mmol) was then added into the tube. The tube was then vacuumed and introduced by nitrogen. 30 mL of DMF was then added into the tube, and the mixture in the tube was heated to 160° C. and stirred for 20 hours. The reaction result was extracted by supersaturated saline and ethyl ether to collect an organic phase. The organic phase was dehydrated by magnesium sulfate, and then concentrated by a rotary evaporator. The concentrated substance was purified by chromatography with an eluent of dichloromethane and n-hexane (v/v=5/1), thereby obtaining 0.8 g of a yellow solid (yield=40%). The above reaction is shown in Formula 17. The spectra of the product in Formula 17 are listed below: $^1$H NMR (400 MHz, CDCl$_3$): δ 8.09 (d, J=8 Hz, 4H), 7.83 (d, J=8 Hz, 4H). $^{13}$C NMR (100 MHz, CDCl$_3$, δ): 190.8, 135.3, 132.9, 130.4, 118.4, 117.4.

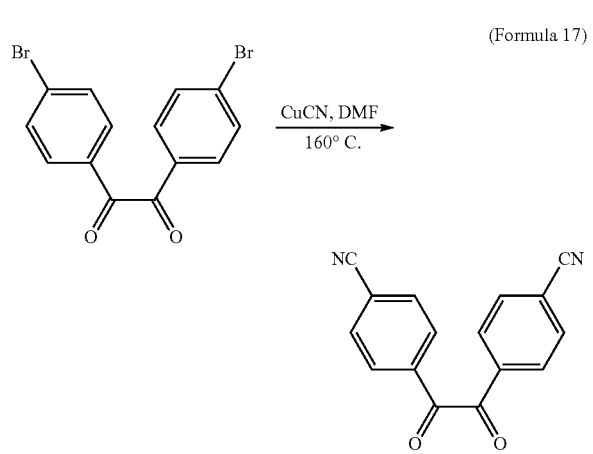

(Formula 17)

1,2,4,5-Benzenetetramine tetrahydrochloride (0.5 g, 1.76 mmol, and commercially available from Alfa Aesar) and the product in Formula 17 (1 g, 3.85 mmol) were put into a reaction bottle. Sodium acetate (0.576 g, 7.02 mmol) and n-butanol (50 mL) were added into the bottle. The mixture in the bottle was heated to 120° C. to react for 20 hours. A yellow precipitate was formed in a solution of the reaction result, and the yellow precipitate was then collected by filtering. The filtered cake was washed by n-hexane and ethyl ether, and then purified by thermal sublimation to obtain 0.8 g of a bright yellow powder (yield=25%). The above reaction is shown in Formula 18. The spectra of the product in Formula 18 are listed below: $^1$H NMR (400 MHz, CDCl$_3$): δ 9.08 (s, 2H), 7.72 (s, 16H). HRMS (EI, m/z): cald. for C38H18N8: 586.1654, Found: 586.1649 (M+).

(Formula 18)

The product in Formula 18 had an Eg of 2.8 eV, a HOMO value of −7.2 eV, and a LUMO value of −4.4 eV, which were measured and calculated by methods that were similar to those of Example 2.

Example 4

2,3-Dichloro-1,4-naphthoquinone (4.54 g, 20 mmol, and commercially available from Alfa Aesar) and potassium phthalimide (15.54 g, 84 mmol) were put in a reaction bottle. 100 mL of acetonitrile was then added into the bottle, and the mixture in the bottle was heated to 85 to react for 3 hours. A yellow precipitate was formed in a solution of the reaction result, and the yellow precipitate was then collected by filtering. The filtered cake was washed by water and methanol to obtain yellow powder (yield=97%). The above reaction is shown in Formula 19. The spectra of the product in Formula 19 are listed below: $^1$H NMR (400 MHz, CDCl3): δ 8.21 (m, 2H), 7.86 (m, 4H), 7.83 (m, 2H), 7.75 (m, 4H).

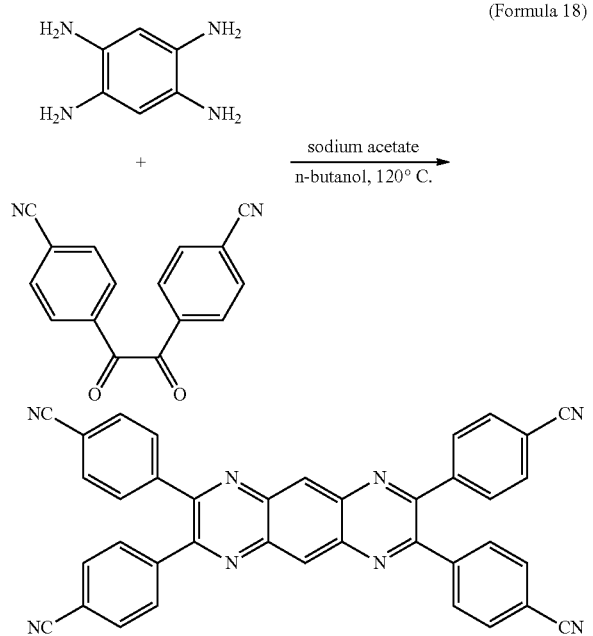

(Formula 19)

The product in Formula 19 (2.24 g, 5 mmol) was put in a reaction bottle. 20 mL of hydrazine hydrate and 150 mL of water were added into the reaction bottle, and the mixture in the bottle was heated to 70° C. to react for 3 hours. A purple precipitate was formed in a solution of the reaction result, and the purple precipitate was then collected by filtering. The filtered cake was washed by water and ethyl ether to obtain purple solid (yield=70%). The above reaction is shown in Formula 20. The spectra of the product in Formula 20 are listed below: $^1$H NMR (400 MHz, CDCl$_3$): δ 8.21 (m, 2H), 7.86 (m, 4H), 7.83 (m, 2H), 7.75 (m, 4H).

(Formula 20)

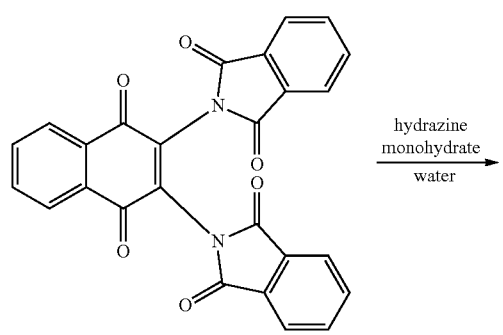

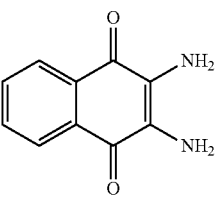

The product in Formula 20 (0.1 g, 0.5 mmol) and the product in Formula 17 (0.138 g, 0.53 mmol) were put in a high-pressure tube. Acetic acid was added into the bottle, and the mixture in the bottle was heated to 75° C. to react for 20 hours. A yellow precipitate was formed in a solution of the reaction result, and the yellow precipitate was then collected by filtering. The filtered cake was washed by water and ethyl ether, and then purified by thermal sublimation to obtain 0.15 g of yellow powder (yield=35%). The above reaction is shown in Formula 21. The spectra of the product in Formula 21 are listed below: $^1$H NMR (400 MHz, CDCl$_3$): δ 8.45 (m, 2H), 7.93 (m, 2H), 7.71 (dd, J=8.4, 18 Hz, 8H). $^{13}$C NMR (100 MHz, CDCl$_3$, δ): 180.5, 154.9, 142.7, 140.5, 135.4, 133.1, 132.6, 130.7, 128.1, 117.8, 114.4. HRMS (EI, m/z): cald. for C26H12N4O2: 412.0960, found: 412.0961 (M+).

(Formula 21)

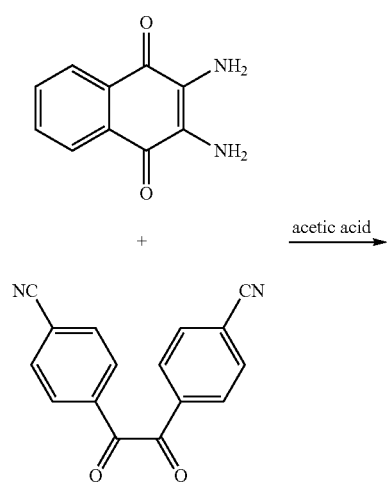

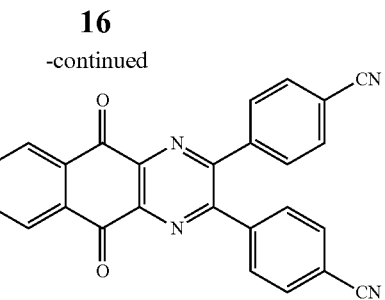

The product in Formula 21 had an Eg of 3.4 eV, a HOMO value of −7.5 eV, and a LUMO value of −4.1 eV, which were measured and calculated by methods that were similar to those of Example 2.

Example 5

The product in Formula 21 (0.15 g, 0.24 mmol) was put into a reaction bottle. The bottle was vacuumed and purged by nitrogen. Anhydrous dichloromethane (5 mL) and malonienitrile (0.063 mL) were then added into the bottle. Anhydrous titanium tetrachloride (0.22 mL) was then added into the bottle in ice bath, and anhydrous pyridine (0.66 mL) was then slowly injected into the bottle. The mixture in the bottle was then stirred for 15 minutes and the ice bath was removed. The mixture was then left at room temperature to react at room temperature for 24 hours. The reaction result was neutralized by dilute hydrochloric acid, and the neutralized substance was extracted by dichloromethane to collect an organic phase. The organic phase was dehydrated by magnesium sulfate and then concentrated by a rotary evaporator. The concentrated substance was purified by chromatography with an eluent of dichloromethane, thereby obtaining a yellow solid. The yellow solid was further purified by thermal sublimation to obtain 0.035 g of dark green powder (yield=24.3%). The above reaction is shown in Formula 22. The spectra of the product in Formula 22 are listed below: $^1$H NMR (400 MHz, CDCl$_3$): δ 8.57 (m, 2H), 7.88 (m, 2H), 7.76 (dd, J=8.8, 42 Hz, 8H). HRMS (EI, m/z): cald. for C32H12N8: 508.1185, found: 508.1187 (M+).

(Formula 22)

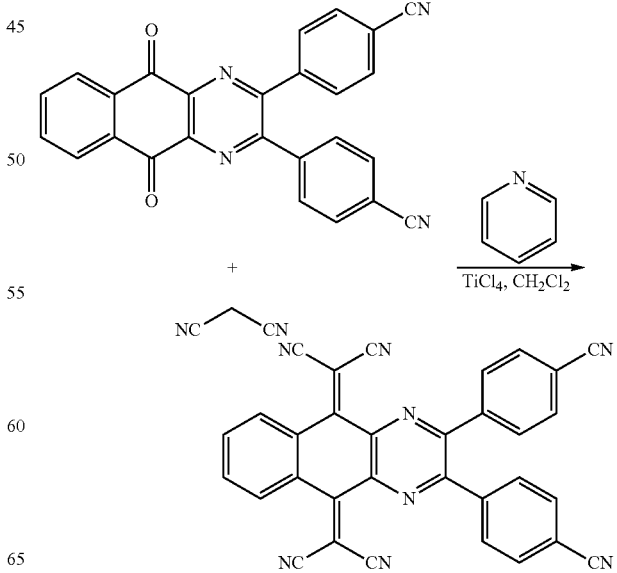

The product in Formula 22 had an Eg of 3.0 eV, a HOMO value of −7.2 eV, and a LUMO value of −4.2 eV, which were measured and calculated by methods that were similar to those of Example 2.

While the disclosure has been described by way of example and in terms of the preferred embodiments, it is to be understood that the disclosure is not limited to the disclosed embodiments. On the contrary, it is intended to cover various modifications and similar arrangements (as would be apparent to those skilled in the art). Therefore, the scope of the appended claims should be accorded the broadest interpretation so as to encompass all such modifications and similar arrangements.

What is claimed is:

1. A carrier generation material, having a chemical structure of:

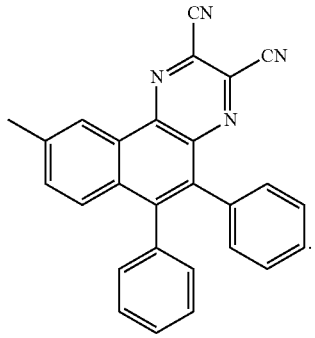 [SMILES: Cc1ccc2c(-c3ccccc3)c(-c3ccccc3)c3nc(C#N)c(C#N)nc3c2c1 ; "."]

2. An organic light-emitting diode, comprising:
    an anode;
    a cathode;
    a carrier generation material layer, including the carrier generation material as claimed in claim 1, disposed between the anode and the cathode;
    a first light-emitting layer disposed between the anode and the carrier generation material layer; and
    a second light-emitting layer, disposed between the cathode and the carrier generation material layer.

3. A carrier generation material, having a chemical structure of:

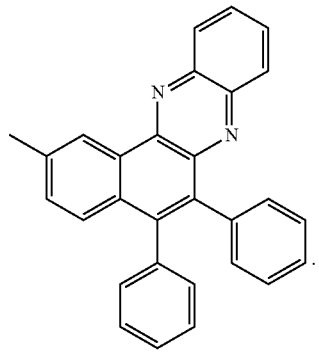 [SMILES: Cc1ccc2c(-c3ccccc3)c(-c3ccccc3)c3nc4ccccc4nc3c2c1]

4. An organic light-emitting diode, comprising:
    an anode;
    a cathode;
    a carrier generation material layer, including the carrier generation material as claimed in claim 3, disposed between the anode and the cathode;
    a first light-emitting layer disposed between the anode and the carrier generation material layer; and
    a second light-emitting layer, disposed between the cathode and the carrier generation material layer.

* * * * *